(12) United States Patent
Trotter

(10) Patent No.: US 6,429,154 B1
(45) Date of Patent: Aug. 6, 2002

(54) BACKING MATERIAL FOR PLASTERS AND DRESSINGS

(75) Inventor: Sebastian Trotter, Buchholz (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/261,694

(22) Filed: Mar. 3, 1999

(30) Foreign Application Priority Data

Apr. 8, 1998 (DE) .......................................... 198 15 762

(51) Int. Cl.[7] .......................... B32B 27/12; B32B 27/04; B32B 27/02; D03D 9/00
(52) U.S. Cl. ............................. 442/45; 442/38; 442/43; 442/46; 442/49; 156/60
(58) Field of Search .............................. 442/38, 43, 45, 442/46, 49; 156/60

(56) References Cited

U.S. PATENT DOCUMENTS 5,633,070 A * 5/1997 Murayama et al. ......... 428/194

FOREIGN PATENT DOCUMENTS

DE 4007891 A * 9/1991 ........... B32B/27/12

* cited by examiner

*Primary Examiner*—Terrel Morris
*Assistant Examiner*—Ula C. Ruddock
(74) *Attorney, Agent, or Firm*—Norris McLaughlin & Marcus

(57) ABSTRACT

Backing material for medical purposes consisting of a laminate comprising a first polymeric film layer, a flexible net film and an at least partially applied self-adhesive coating, the net film being partly embedded in the self-adhesive coating and so anchored therein.

9 Claims, No Drawings

BACKING MATERIAL FOR PLASTERS AND DRESSINGS

BACKING MATERIAL FOR PLASTERS AND DRESSINGS

The invention relates to a flexible multilayer laminate for use as a backing material in plasters and wound coverings which can be applied without auxiliary supports.

Flexible backing materials are preferentially employed when plasters are intended, following their application, to follow movements of the body without presenting too great a resistance.

DE 43 14 834 C2 discloses a film-based dressing material which is covered on one side with a backing material having the same size as the film and having at least one gripping strip and which on the other side is provided with a self-adhesive layer. The gripping strips in this arrangement are disposed within the peripheral bounds of the material. The film consists preferably of polyurethane and the backing material of polyethylene.

When the dressing material is applied, the backing material is removed from the film—which remains adhering on the skin by virtue of the self-adhesive layer—by means of the gripping strips.

Especially when used in the region of the joints, the advantages of products as provided in DE 43 14 834 C2 in terms of flexibility are known. Furthermore, the use of PU backing films brings about high water vapour permeability.

However, the product design has a large number of disadvantages. The gripping strips provided for removing the auxiliary support give rise to additional waste and high costs, and proper application, i.e. the need to remove the auxiliary support, is not always understood ad hoc by the customer. Furthermore, the inflexible auxiliary support frequently stands in the way of creaseless and hence watertight and germtight application to, for example, the finger. Finally, the auxiliary backing is a disruption in the case of an overlap, especially on application to the finger. A comparable dressing material is known from DE 40 26 755 A. Here, however, the backing material has two gripping strips which project beyond the dressing material.

DE 40 07 891 A discloses a backing material for medical purposes which consists of a laminate which in turn is composed of a first polymeric film layer, a second polymeric film layer produced on the first layer, and a third layer which is at least partly embedded in the second layer and comprises a macroporous textile material.

EP 0 673 657 A1 describes a further laminate which is composed of three layers. A self-adhesive coating is applied to one side of a nonwoven. Finally, on the opposite side of the nonwoven, a water vapour permeable and substantially water-impermeable film is applied.

The object of the invention was to avoid the disadvantages of the prior art or at least to lessen them. In particular, the object of the invention is to provide a backing material for medical purposes which is highly flexible and permeable to water vapour and yet is of high strength.

This object is achieved by means of a backing material for medical purposes which consists of a laminate, as characterized further in the main claim. The subclaims relate to particularly advantageous embodiments of the laminate. The invention additionally provides a process for preparing the laminate.

The invention relates accordingly to a backing material for medical purposes, consisting of a laminate comprising a first polymeric film layer, a flexible net film and an at least partially applied self-adhesive coating, the net film being partly embedded in the self-adhesive coating and so anchored therein.

There is preferably a second polymeric layer between the first polymeric layer and the self-adhesive coating.

It has been found advantageous for the first and the second polymeric layers to consist of an elastic aliphatic polyester-polyurethane.

It is also advantageous if the first and second polymeric layers each have a thickness of from 0.005 to 0.035 mm.

The net film consists preferably of polyethylene, polypropylene, polyamide, polyurethane, EVA, polystyrene (including high impact polystyrene (HIPS)), or compositions of the said polymers. In addition, the net film may also be colored, in order to give particular optical effects to the laminate.

The net film preferably has the following characteristics:
a thickness from 0.01 to 0.07 mm
a basis weight from 5 to 40 g/m$^2$
on open area from 30% to 70%, and/or
a mesh size from 0.3 to 1.5 mm.

In order to ensure the required stability of the laminate, the self-adhesive coating should be applied with a weight per unit area of from 20 to 100 g/m$^2$.

The backing material of the invention is particularly suitable for producing plasters with or without a wound pad on the self-adhesive coating.

Finally, the invention also embraces a process for preparing the backing material. According to this process, first of all, the first polymeric layer is produced on an auxiliary support. If desired, the second polymeric layer is produced on the first layer.

In parallel to this, an intermediate support which has been given an anti-adhesive treatment is coated at least partly with the adhesive composition in the form of a solution, dispersion or melt, the said intermediate support being, for example, a siliconized kraft paper or a siliconized film, and then the net film is laminated or laid in the still liquid adhesive composition.

In this procedure, the net film sinks to a greater or lesser depth into the still solvent-containing mass or still liquid melt. In the drying tunnel, the solvent evaporates and the adhesive composition surrounds the net film, so that the assembly solidifies, in the case of a hotmelt adhesive, the assembly solidifies through cooling of the adhesive composition.

This is followed by the lamination of the first and, if present, second polymeric layer to the intermediate laminate comprising net film, adhesive coating and intermediate support, with the resulting laminate also being solidified, especially by means of calendar treatment.

It necessary, the composition is crosslinked by means of UV radiation, etc. The intermediate support used to produce the first and second polymeric layers is delaminated and the web of material can be wound on itself and subsequently cut to mother rolls of the desired width. Thereafter, the material is made up into ready-to-use single products with or without a wound pad, and the end product is y-sterilized if desired.

The backing material of the invention provides a laminate in which the flexible PU film is supported by a flexible net film incorporated into the adhesive composition, this support being such that application without an auxiliary backing film is possible and the required product properties are retained.

The laminate has numerous advantages:
1. There is no longer a need for any auxiliary support nor for any gripping strip, which leads to a reduction in cost relative to the products known from the prior art.

2. The user receives a product which can be applied without further explanation.
3. The ease of handling also permits overlaps on application, like a conventional product, when applied, for example, to the finger.
4. The product appears more environment-friendly, since waste is reduced.
5. The new visual appearance (the net can be colored) makes the innovation immediately recognizable and representable.

The intention of the text below is to illustrate the invention with reference to an example without thereby wishing to restrict the invention unnecessarily.

EXAMPLE 1

1a) Preparing the Intermediate Product

A dulled PE film (for example, LDPE Waloplast matt 230 F 80 from Wolff Walsrode) is coated with an anionic aliphatic polyesterpolyurethane dispersion (Impranil® grades from Bayer AG) in a thickness from 0.015 to 0.02 mm and is dried in a tunnel with graded heating at temperatures from 20 to 90° C. to form a blisterless film layer. Subsequently, in the same way and thickness, a further film layer is applied to the existing layer.

1b) Reducing the Net Film/self-adhesive Composition Assembly

A siliconized release film (for example, Trennfolie farblos LF D 70 from Laufenberg) is coated with a UV-crosslinkable self-adhesive composition according to DE P 27 43 979 so as to give a dry film thickness of 50 g/m². Directly downstream of the coating apparatus, a net film (for example, Netz RX 27 from Smith&Nephew) is laid into the liquid self-adhesive composition so that it sinks completely or partly in the solution.

To evaporate the solvent, the entire web is dried in a drying tunnel with graded heating from 20 to 80° C. After leaving the drying tunnel, the intermediate product described under 1a) is laminated by its PU film side to the open side of the selfadhesive composition.

The assembled product is irradiated by means of UV in order to crosslink the self-adhesive composition. Subsequently, the PE auxiliary film is removed and the laminate is wound up into bales. The bales are cut to rolls of different width, the release film still present is removed, a wound pad is laid on, and the material is again lined with release paper. From the resultant web, individual plasters of the desired dimensions are punched and are sealed individually.

I claim:

1. A laminated backing material for medical purposes, comprising a first polymeric film layer, a flexible net film and an at least partially applied self-adhesive coating, the net film being partially embedded in the self-adhesive coating and so anchored therein.

2. Backing material according to claim 1, wherein there is a second polymeric layer between the first polymeric layer and the self-adhesive coating.

3. Backing material according to claim 1, wherein the first and the second polymeric layers consist of an elastic aliphatic polyester polyurethane.

4. Backing material according to claim 1, wherein the first and second polymeric layers have a thickness of from 0.005 to 0.035 mm.

5. Backing material according to claim 1, wherein the net film consists of polyethylene, polypropylene, polyamide, polyurethane, ethylene vinyl acetate, polystyrene, or compositions comprising said polymers.

6. Backing material according to claim 1, wherein the net film has a thickness from 0.01 to 0.07 mm a basis weight from 5 to 40 g/m² an open area of 30 to 70%, and/or a mesh size from 0.3 to 1.5 mm.

7. Backing material according to claim 1, wherein the self-adhesive coating is applied with a weight per unit area of from 20 to 100 g/m².

8. Backing material according to claim 1, wherein plasters are punched from the backing material and these plasters may, if desired, have a wound pad on the self-adhesive coating.

9. Process for producing a backing material according to claim 1, in which the first polymeric layer is produced on an auxiliary support, and optionally the second polymeric layer is then produced on the first layer, the adhesive composition is applied at least partly to an intermediate support which has been given an anti-adhesive treatment, the net film is laminated into the still liquid adhesive composition, the first or second polymeric layer, respectively, is laminated together with the intermediate laminate comprising net film, adhesive coating and intermediate support, and the resultant laminate is consolidated.

* * * * *